(12) United States Patent
Yanai et al.

(10) Patent No.: US 6,713,618 B1
(45) Date of Patent: Mar. 30, 2004

(54) DNA WHICH ENCODES TREHALASE AND USES THEREOF

(75) Inventors: Yoshiaki Yanai, Okayama (JP); Harumi Ariyasu, Okayama (JP); Tsunetaka Ohta, Okayama (JP); Masashi Kurimoto, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 09/578,921

(22) Filed: May 26, 2000

(30) Foreign Application Priority Data

May 26, 1999 (JP) ............................................. 11-147284

(51) Int. Cl.$^7$ ........................ C07H 21/04; C07H 21/02; C12P 21/06; C12P 21/04; C12P 5/00
(52) U.S. Cl. ................. 536/23.51; 435/325; 435/252.3; 435/183; 435/69.1; 435/70.1; 435/71.1; 536/23.1
(58) Field of Search .............................. 536/23.1, 23.4, 536/23.5; 435/320.1, 325, 183; 530/300, 350

(56) References Cited

FOREIGN PATENT DOCUMENTS

| EP | 0 606 753 | 7/1994 |
|----|-----------|--------|
| EP | 0 628 630 | 12/1994 |
| JP | 7 143876 | 6/1995 |
| JP | 7 213283 | 8/1995 |

OTHER PUBLICATIONS

M Marra et al., Locus Accession No. AW044983,Sep. 1999.*
R Ishihara et al., Elsevier Science, "Molecular cloning, sequencing and expression of cDNA encoding human trehalase,"1997, (202), pp. 69–74.*
TJ Oesterreicher et al., Am. J.Physiol.,"Rat trehalase: cDNA cloning and mRNA expression in adult rat tissues and during intestinal ontogeny," 1998, 274,43:R1220–R1227.*
Migone et al. Proc Natl Acad Sci U S A. Mar. 31, 1998;95(7):3845–50. Recruitment of SH2–containing protein tyrosine phosphatase SHP–1 to the interleukin 2 receptor; loss of SHP–1 expression in human T–lymphotropic virus type I–transformed T cells.*
Oesterreicher et al., "Rat trehalase: cDNA cloning and MRNA expression in adult rat tissues and during intestinal ontogeny", *American Journal of Physiology*, (1998), vol. 274, No. 5 part 2, pp. 1220–1227.
Ishihara et al., "Molecular cloning, sequencing and expression of cDNA encoding human trehalose", *Gene*, (1997), vol. 202, pp69–74.
Baumann et al., "Trehalose activity in genetically diabetic mice (serum, kidney and liver)", *Journal of Medical Genetics*, (1981), vol. 18, pp. 418–423.
Abstract Database EBI Online, "Mus musculus trehalase mRNA", Apr. 4, 2000.
Abstract Oesterreicher et al., "Structure and Hormonal Regulation of the Mouse Trehalase Gene", *Gastroenterology*, (2000), vol. 118, No. 4, pp. 1640.
Oku et al., "Trehalose Content in Foods", *Journal of the Japanese Society for Food Science and Technology*, vol. 45, No. 6, pp. 381–384, (1998) abstract only.
Hay et al., American Type Culture Collection Catalogue of Cell Lines and Hybridomas Seventh Edition, (1992).
Ausubel et al., "Current Protocols in Molecular Biology" contents listing only.
Muramatsu et al., "New Genetic Engineering Handbook", translation p 269, In 25–p 270 In 20.

* cited by examiner

Primary Examiner—Deborah J. Reynolds
Assistant Examiner—Joseph Woitach
(74) Attorney, Agent, or Firm—Browdy and Neimark

(57) ABSTRACT

Disclosed are a DNA which encodes murine trehalase, a polypeptide expressed by the DNA, and a transgenic- and knockout- animals which have been genetically engineered with the DNA. The DNA comprises a part or the whole of the nucleotide sequence of SEQ ID NO:1.

15 Claims, No Drawings

DNA WHICH ENCODES TREHALASE AND USES THEREOF

BACKGROUND OF THE INVENTION

1. Field of the Invention

The present invention relates to a novel DNA, more particularly, to a novel DNA which encodes trehalase, and uses thereof.

2. Description of the Prior Art

Trehalose, a non-reducing disaccharide which consists of glucose units as constituent saccharide, is widely distributed in the natural world, for example, in bacteria, fungi, algae, insects, Crustacean, etc. In organisms such as insects which have a relatively-large amount of trehalose in their bodies, trehalose would play an important role as energy source and relate to the maintenance of physiological function such as cold resistance. Mammals including humans have long been utilizing trehalose widely from mushrooms, seaweeds, fermented foods, etc, as reported by Oku et al., in "*Journal of The Japanese Society For Food Science And Technology*", Vol. 45, No. 6, pp. 381–384 (1998). As disclosed in Japanese Patent Kokai Nos. 143,876/95 and 213,283/95 applied for by the present applicant, the establishment of technologies for industrial-scale production of trehalose has more increased the interest of trehalose in the maintenance and regulation of biological functions in mammals, and this results in energetic and continuous researches in various fields.

Trehalase is an enzyme which specifically hydrolyzes the glucosidic bond in trehalose. Because of this substrate specificity, the enzyme may deeply correlate to the trehalose level in vivo in organisms such as insects and relate to the regulation of their biological functions. Even in mammals with no significant amount of trehalose, trehalase is found in animals such as humans, mice and rats. Major physiological role of trehalase in mammals would be the hydrolysis of externally-ingested trehalose when the saccharide is digested and absorbed by the mammals. It was reported that trehalase is commonly found in specific mammalian organs independently of the intake of trehalose, and hence there still remains many unknown biological roles of trehalase per se. As described above, the roles of mammalian trehalase in the maintenance and regulation of their physiological functions have also been focused recently, along with the increasing interest in trehalose.

Methods in a molecular biological manner are very useful for elucidating the physiological roles of specific enzymes or polypeptides in living bodies. Mice are the animals commonly used widely as models for elucidating the biological functions of mammals including humans. Thus, the techniques and analyses for murine trehalase in a molecular biological manner would be particularly useful for elucidating the physiological roles of mammalian trehalase. Any nucleotide sequence of murine trehalase, which is requisite for its molecular biological engineering, has not been elucidated, and any structure of the enzyme per se has not been disclosed. Urgently expected are as follows: The elucidation of a nucleotide sequence of a DNA for murine trehalase, the establishment of a DNA useful for engineering the enzyme in a molecular biological manner, and uses thereof.

SUMMARY OF THE INVENTION

In view of the foregoing, the object of the present invention is to provide a DNA useful for engineering murine trehalase in a molecular biological manner, and uses thereof.

To attain the above object, the present inventors widely screened cDNAs for RNAs, collected from mice, to isolate a cDNA for murine trehalase. As a result, the present inventors obtained from a murine intestine a cDNA which consists of about 2,000 base pairs (hereinafter abbreviated as "bp") and expresses a polypeptide with trehalase activity. When compared with nucleotide sequences of conventionally known DNAs, the cDNA contained, as a coding sequence of the polypeptide, a nucleotide sequence of SEQ ID NO: 1 which was clearly different from conventionally known DNAs. The present inventors also found the fact that a gene for the cDNA exists on a murine chromosome. Based on these results, they confirmed that the cDNA was for murine trehalase, and then analyzed murine genomic DNAs with reference to the nucleotide sequence of the cDNA, elucidated the structure of a gene for murine trehalase which consists of a total length of about 20,000 bp and comprises the nucleotide sequence of SEQ ID NO: 1 and introns for splitting the nucleotide sequence, and isolated the gene as a genomic DNA. The present inventors also confirmed that a part or the whole of the isolated DNA can be arbitrarily used to engineer and analyze murine trehalase in a molecular biological manner. For example, such a DNA can be advantageously used to prepare transformants suitable for producing polypeptides used as murine trehalase standard specimens and as antigens for preparing anti-murine trehalase antibodies, and to prepare transgenic animals and trehalase gene knockout animals. The present invention is based on these findings.

The present invention solves the above object by providing a DNA which comprises a part or the whole of the nucleotide sequence of SEQ ID NO: 1 that encodes trehalase, a polypeptide obtainable by the expression of the DNA, a process for producing the polypeptide using the DNA, and a transgenic- and knockout-animals obtainable therewith.

DETAILED DESCRIPTION OF THE INVENTION

The present invention relates to a novel DNA which encodes trehalase and uses thereof. The term "trehalase" as referred to in the present invention means an enzyme, i.e., a protein or polypeptide which specially hydrolyzes the glucosidic bond in α,α-trehalose, and the hydrolysis activity is called "trehalase activity" in the present invention. The DNA of the present invention comprises a part or the whole of the nucleotide sequence of SEQ ID NO: 1 which encodes trehalase, and usually it is mouse origin.

In the present invention, the term "a part or the whole of the nucleotide sequence of SEQ ID NO: 1" generally means "a nucleotide sequence which contains at least ten and several contiguous bases in the nucleotide sequence of SEQ ID NO: 1."

Preferred examples of the DNA of the present invention include DNAs as cDNAs which comprise a part or the whole of the nucleotide sequence of SEQ ID NO: 1, DNAs as genomic DNAs obtainable by fragmenting chromosomes, and other DNAs obtainable by applying replacement, deletion, and/or addition of bases to the above DNAs. These DNAs do not contain telomeres as a characteristic structure in the terminal region of chromosomes of eukaryotic cells such as mammalian cells, and such DNAs are usually provided in the from of isolated liner DNAs which are composed of not more than about 20,000 bp and which are distinguishable from naturally-occurring chromosomal DNAs and RNAs present in mammalian cells. All of these DNAs according to the present invention may be homologous to the nucleotide sequences of cDNAs for human and rat trehalases, registered in "GenBank", a database of nucleic acids provided by the National Institute of Health of USA, under the accession Nos. AB000824 and AF038043, respectively, but are not completely coincided with the above registered nucleotide sequences.

A cDNA, as an example of the DNA of the present invention, usually comprises a part or the whole of the nucleotide sequence of SEQ ID NO: 1 as a coding sequence or nucleotide sequence which encodes the polypeptide of the present invention, and may contain a nucleotide sequence as a non-coding region at the 5' and/or 3' end regions. Usually, such a cDNA can be obtained by preparing in the usual manner a cDNA using a RNA as a template obtainable from organs such as intestines, kidneys, livers, and lungs from mice or their relative rodents, and cell lines established from these organs; and screening the cDNA with an index of the existence of annealing with at least a part of the nucleotide sequence of SEQ ID NO: 1. Any method such as PCR, colony hybridization, or plaque hybridization method commonly used in this art can be used as the screening method. Although the DNAs thus obtained are varied depending on the nature of species, strains, individuals, and organs as RNA sources, such DNAs are clearly homologous to the nucleotide sequence of SEQ ID NO: 1, usually they have a homology of over 94%, more desirably, 97% or higher. For example, as described in the later described examples, a DNA, which has the nucleotide sequence of SEQ ID NO: 3 and includes the nucleotide sequence of SEQ ID NO: 1, is generally obtained by using RNAs from ddY murine intestines as materials.

A genomic DNA, as another form of the DNA of the present invention, generally contains a part or the whole of the nucleotide sequence of SEQ ID NO: 1 as a coding region, and another nucleotide sequence as an intron and non-translated region. For example, the genomic DNA can be obtained by applying PCR using, as templates, chromosomes obtainable from appropriate organs and cells of mice and their relative rodents; and oligonucleotides as primers prepared based on the nucleotide sequence of SEQ ID NO: 1; or by engineering genomic libraries from the chromosomes in the usual manner, and screening the desired DNAs using a probe prepared based on the nucleotide sequence of SEQ ID NO: 1. Depending on the nature of species, strains, individuals, and organs of the sources of chromosomes, the DNAs thus obtained may be varied in some degrees with respect to the nucleotide sequence of a coding sequence, non-translated region, and/or intron. The DNAs, however, have a clear homology to the nucleotide sequence of SEQ ID NO: 1, usually, a homology of over 94%, more preferably, 97% or higher. For example, a chromosome from ICR Swiss mouse provides a DNA which comprises both the nucleotide sequence of SEQ ID NO: 1 and at least an intron that exists between the bases 80 and 81 in the nucleotide sequence. From a chromosome of C57BL/6 mouse, the following DNA can be obtained: A DNA which comprises the nucleotide sequence of SEQ ID NO: 1 and at least the introns which exist respectively between the bases 181 and 182, 326 and 327, 414 and 415, 515 and 516, 608 and 609, 725 and 726, 848 and 849, 898 and 899, 1093 and 1094, 1311 and 1312, 1423 and 1424, 1536 and 1537, and 1590 and 1591 in the nucleotide sequence of SEQ ID NO: 1. The above genomic DNA according to the present invention can be usually obtained as a liner DNA which consists of about 20,000 bases or fewer.

As described above, the isolated DNA of the present invention can be made modifications such as fragmentation, replacement, deletion, and/or addition of bases by conventional methods used in this art. The DNA of the present invention includes the aforesaid modified DNAs as long as they contain at least a part of the nucleotide sequence of SEQ ID NO: 1. For example, single-stranded DNAs or oligonucleotides, which consist of at least ten and several contiguous bases in the sense or anti-sense strand of the above DNAs, are useful as PCR primers and hybridization probes to detect or amplify the DNA of the present invention. The oligonucleotides can also be used to detect and amplify trehalase-related DNAs, which comprise a part of the nucleotide sequence of SEQ ID NO: 1, other than those illustrated in the present specification. The oligonucleotides as PCR primers can be incorporated with other nucleotide sequences such as restriction-enzyme-recognizing sites, and modified by replacement, deletion, and/or addition of bases with or without altering the amino acid sequence encoded by the oligonucleotides. The DNAs as PCR primers, which have been received with any of the above modifications, can be arbitrarily used to prepare recombinant DNAs as expression vectors for expressing trehalase and as targeting vectors for preparing knockout mice. These DNAs in the form of oligonucleotides can be obtained by chemical-synthetic-methods which are commonly used in this art.

By applying conventional PCR reaction to the above DNAs, the following DNAs can be obtained: DNAs which consist essentially of at least a part of the coding sequences for the above exemplified DNAs, for example, those which consist of either the nucleotide sequence of SEQ ID NO: 1 or bases 58 to 1728 in the nucleotide sequence of SEQ ID NO: 1, and nucleotide sequences which are partial nucleotide sequences of SEQ ID NO: 1 and which correspond to amino acid sequences that consist of at least ten contiguous amino acids. For example, by using the recombinant DNA technology, these DNAs can be arbitrarily used to produce murine trehalase-related polypeptides used as standard specimens for qualitative- and quantitative-analyses of murine trehalase, and as antigens for preparing anti-murine trehalase antibodies. In the case of expressing the aforesaid DNAs, replacement, addition, and/or deletion of bases can be further introduced into a part of the DNAs, depending on the hosts used. Examples of such modifications are as follows:

(i) Replacement of a part of the bases of the DNAs with reference to the frequency of codons used in host cells without altering the inherent amino acid sequences encoded by the DNAs;

(ii) Addition of initiation and termination condons to the DNAs;

(iii) Addition of nucleotide sequences recognizable by specific substances such as histidine tag to the N- or C-terminus of polypeptides to be expressed;

(iv) Deletion of a part of the bases of the DNAs in the 5' or 3' end region to increase the efficiency of DNA expression; and (v) Insertion of one or more of the above introns into suitable sites in the DNAs.

These DNAs of the present invention comprise the nucleotide sequences which usually have a homology of over 94%, more preferably, 97% or higher to the sequence which consists of at least about 30 contiguous bases in the nucleotide sequence of SEQ ID NO: 1. The DNA of the present invention includes those in the form of a recombinant DNA and those introduced into appropriate host cells.

The present invention provides a polypeptide obtainable by the expression of any of the above DNAs. The polypeptide of the present invention comprises an amino acid sequence which has a homology of 94% or higher, more preferably, 97% or higher to an amino acid sequence which consists of ten and several contiguous amino acids in the amino acid sequence of SEQ ID NO: 2: and may have trehalase activity. For example, an amino acid sequence, which consists of about 20 amino acids in the N-terminal region of the amino acid sequence of SEQ ID NO: 2, is capable of functioning as signal peptide; and another animo acid sequence, which consists of amino acids 20 to 576 in the amino acid sequence where the signal peptide has been eliminated, can participate in the expression of trehalase activity. The polypeptide of the present invention can be obtained in a desired amount by the following process of the present invention, which comprises the steps of producing the polypeptide from cells capable of producing the polypeptide of the present invention, i.e., a polypeptide which comprises at least a part of the amino acid sequence encoded by the nucleotide sequence of SEQ ID NO: 1; and collecting the produced polypeptide. Transformants, which have been introduced with any of the above DNAs that consist essentially of at least a part of the coding sequence, are particularly useful as the cells used in the process of the present invention. These transformants can be usually obtained by annealing any of the above DNAs with autonomously-replicable vectors into recombinant DNAs, and introducing the DNAs into appropriate hosts. The autonomously-replicable vectors can be selected from conventional plasmid vectors such as pCDM8, pcDNAI/Amp, pcDL-SR α, BCMGSNeo, pSV2-neo, pSV-2gpt, pEF-BOS, pCEV4, pME18S, pKY4, pKK223-3, pVL1392, and pVL1393. In general, the replicable vectors contain appropriate nucleotide sequences, which allow the DNA of the present invention to express in each hosts, such as promoters, enhancers, replication origins, termination sites, and splicing- and/or selective-sequences. Any method conventionally used in this art can be selectively used to ligate the DNA of the present invention to the above vectors. For example, addition of linkers or sequences for recognizing restriction enzymes by PCR, and treatment of restriction enzymes or ligases are all useful.

Any cells derived from microorganisms, plants, and animals including vertebrates such as mammals and invertebrates such as insects, which are all commonly used in this art to prepare transformant cells, can be used as host cells to be introduced with the DNA of the present invention. To prepare the polypeptide of the present invention at a lesser cost and in a relatively-high yield, microorganisms such as *Escherichia coli* and *Bacillus subtilis*, and cells from insects can be preferably used as hosts. Eukaryotic cells from yeasts and animals can be preferably used when the polypeptide is directed to use in the field of reagents for researches or pharmaceuticals for mammals which require a polypeptide equivalent to the one present naturally in the murine body with respect to saccharide chains to be added to and intra- and extra-cellar locations of the polypeptide. Examples of such host cells from animals include COS-1 cells (ATCC CRL-1650), CHO-K1 cells (ATCC CCL-61), 3T3-Swiss albino cells (ATCC CCL-92), C127I cells (ATCC CRL-1616), CV-1 cells (ATCC CCL-70), HeLa cells (ATCC CCL-2), MOP-8 cells (ATCC CRL-1709), and variants thereof; epithelial cells from humans, monkeys, mice, and hamsters; stromal cells; hematopoietic cells; and cells from insects such as Sf9 cells, commercialized by BD PharMingen, 10975 Torreyana Road, San Diego, Calif. 92121, USA, and High Five cells, commercialized by Invitrogen BV, NV Leek, Netherlands. To introduce the DNA of the present invention into the above host cells, any of the following conventional methods can be used; DEAE-dextran method, calcium phosphate method, electroporation, lipofection method, microinjection method, and virus infection method using retrovirus, adenovirus, herpes virus, or vaccinia virus. Desired clones can be selected from the resulting transformants with an index of the existence of an introduced DNA or the productivity of the polypeptide. With regard to the aforesaid recombinant DNAs and transformants, materials and methods commonly used in this art are described in detail in "*Current Immuno-protocol in Molecular Biology*", chapters 1–9 and 15–16 (1996), edited by Frederick M. Ausubel et al., published by John Wiley and Sons Inc., New York, U.S.A.

The transformants thus obtained produce the polypeptide of the present invention intra- or extra-cellularly by culturing or proliferating in media under the conditions selected depending on the type of host cells or the structure of vectors used to introduce the DNA of the present invention. Although, the produced polypeptide can be used intact to suit to final use, it is usually purified before use. For the purification, any conventional methods commonly used in this art can be used, for example, salting out, dialysis, filtration, concentration, fractional precipitation, ion-exchange chromatography, gel filtration chromatography, absorption chromatography, isoelectric chromatography, hydrophobic chromatography, reverse phase chromatography, affinity chromatography, gel electrophoresis, and isoelectric electrophoresis. The polypeptide of the present invention, purified to a desired level, can be obtained by allowing the resulting fraction, which has been purified by the above purification methods, to examine and analyze properties such as amino acid sequence, molecular weight, and trehalase activity of the polypeptide; and collecting a fraction which exhibits the desired properties.

In this art, once a desired DNA is obtained, it can be commonly introduced into appropriate animals to obtain so called transgenic animals. The present invention also provides transgenic animals by applying conventional methods to the DNA of the present invention. The transgenic animals can be generally prepared by introducing the DNA, which comprises at least a part of the aforesaid coding sequence, into appropriate vectors which are selected depending on the species of the hosts used, in combination with another desired nucleotide sequences for promotors or enhancers, etc., if necessary; and introducing the resulting recombinant DNA into fertilized eggs or embryonic stem cells of host animals by either conventional methods such as microinjection or infection with viruses. The following animals can be advantageously used as host animals in the present invention because they can be bred easily: Rodents such as mice, rats, and hamsters which are used frequently as experimental animals; and other mammals such as goats, sheep, pigs, and cows which are commonly bred as domestic animals. The obtained cells introduced with the DNAs are transplanted to uterines or uterus of female animals in pseudopregnancy, which are the same species as the cells. Transgenic animals introduced with the DNA of the present invention can be obtained by applying hybridization or PCR method to newborns born by natural delivery or Cesarean section, and selecting animals introduced with the DNA. With these methods, the productivity of the polypeptide with trehalase activity of the present invention can be imparted to a desired animal. The transgenic animals thus obtained can be arbitrarily used in the production of the polypeptide of the present invention and also used as animal models for examining the in vivo influence of the polypeptide in living bodies, and used as animals for screening therapeutic, prophylactic, and diagnostic agents for mammalian diseases related to the excessive production of the polypeptide. The techniques for preparing transgenic animals as mentioned above are described in detail in "*New Genetic Engineering Handbook*", pp. 269–276 (1996), edited by Masami MURAMATSU, Hiroto OKAYAMA, and Masashi YAMAMOTO, published by Yodo Co., Ltd., Tokyo, Japan.

In this field, once the gene structure of a desired gene is revealed and a DNA which contains at least a part of the gene is isolated, animals with artificially destroyed genes, i.e., knockout animals can be generally obtained. A general preparation method of a knockout animal is described in the below with reference to a knockout mouse:

(i) Preparing a vector (targeting vector) to destroy a desired gene;

(ii) Introducing the targeting vector into murine embryonic stem cells (ES cells) with totipotency;

(iii) Selecting ES cells where the desired gene has been destroyed by the introduced targeting vector;

(iv) Infecting the selected ES cells into a murine blastula, transplanting the murine blastula to an expedient mouse, and selecting a chimaera mouse from newborns delivered from the expedient mouse;

(v) Inbreeding a male chimera mouse with a female wild-type mouse, and selecting a male and female heterozygotes from F1 mice delivered from the female mouse; and (vi) Inbreeding the male and female heterozygotes, and selecting a homozygote (knockout mouse) from F2 mice delivered from the female mouse.

As mentioned above, since the present invention discloses a DNA as a genomic DNA which corresponds to a trehalase gene that comprises a part or the whole of the nucleotide sequence of SEQ ID NO: 1, knockout animals with a destroyed trehalase gene can be prepared by using the DNA in such a form. The present invention also provides such knockout animals. In the preparation of knockout animals of the present invention, targeting vectors used in the above step (i) are prepared. The targeting vector used in the present invention is generally prepared by applying replacement, deletion, and/or addition of bases to coding sequences of genomic DNAs, which contain at least apart of the nucleotide sequence of SEQ ID NO: 1, to modify the DNAs so as not to encode a polypeptide with trehalase activity, and introducing the modified DNAs into autonomously-replicable vectors. To ease the selection of ES cells in the above step (iii), the targeting vector should preferably be introduced with a sequence as positive and/or negative selective-markers. Concrete examples of the positive selective markers include a neomycin resistant gene and β-galactosidase gene, and those of the negative selective markers include a herpes-simplex-virus-thymidine-kinase gene and a diphtheritic-toxin-A-fragment gene. By using methods such as electroporation, the resulting targeting vector is usually digested with an appropriate restriction enzyme for linearization, and then introduced into animal's ES cells with a desired trehalase gene, usually, into murine ES cells. When homologous recombination occurs in cells which have been introduced with the targeting vector, the trehalase gene inherent to the cells is destroyed by replacing with a nucleotide sequence which is from the targeting vector and free of encoding a polypeptide with trehalose activity. The desired ES cells can be selected by screening the products from the cells introduced with the vector by using conventional methods such as PCR method for confirming the intracellular homologous recombination (the above step (iii)). With the ES cells thus obtained, the knockout animals of the present invention can be obtained by treating the cells in accordance with the above steps (iv) to (vi). The obtained knockout animals are specifically useful as models for examining the in viva physiological role of trehalase and as animals for screening therapeutic, prophylactic, and diagnostic agents for animal diseases correlated to defection or incompletion of trehalase. The preparation method for knockout animals is called gene targeting and reported in detail in "*New Genetic Engineering Handbook*", pp. 277–283 (1996), edited by Masami MURAMATSU, Hiroto OKAYAMA, and Masashi YAMAMOTO, published by Yodo Co., Ltd., Tokyo, Japan.

The preferred embodiments according to the present invention are described in the below with reference to the following Examples, and can be modified or diversified according to the state of the art. In view of the state, the present invention should not be limited to these Examples.

EXAMPLE 1

DNA Encoding Trehalase

EXAMPLE 1-1

Isolation of Partial cDNA from Murine Intestine

The intestines used in this example were prepared from butchered five-week-old ddY female mice whose cervical vertebrates had been dislocated. The intestines were cut lengthwisely, and the inwalls were washed with a physiological saline. Thereafter, epidermal cells of the intestines were taken 1.1 g by wet weight in conventional manner, and then soaked in 7.7 ml of a mixture (pH 7.0) consisting of 5 M guanidine isothiocyanate, 10 mM EDTA, 50 mM Tris-HCl(pH 7.0), and 8 w/v % of 2-mercaptoethanol, disrupted by a homogenizer, and kept at 4° C. for 15 hours to obtain a cell disruptant. According to a conventional manner, to 35-ml centrifugation tubes were added one milliliter aliquots of 100 mM EDTA (pH 7.5) containing 5.7 M cesium chloride, and 10 ml of the cell disruptant was layered on each solution. These tubes were subjected to ultracentrifugation at 25,000 rpm and at 20° C. for 20 hours to obtain precipitates as RNA fractions. To 15-ml centrifugation tubes were added these RNA fractions and equal volumes of a mixture of chloroform and isobutanol (=4:1 by volume), and the tubes were shaken for five minutes and centrifuged at 15,000 rpm and at 4° C. for 10 minutes. The supernatants were mixed with 2.5-fold volumes of ethanol and cooled at −20° C. for two hours to precipitate all RNAs. The precipitates were washed with 75 v/v % aqueous ethanol, and dissolved in 0.5 ml of sterile distilled water to obtain the RNAs, followed by treating the RNAs with "Oligotex-dT30 <SUPER>", an oligo (dT) binding bead commercialized by Takara Shuzo Co., Ltd., Otsu, Shiga, Japan, to collect and purify Poly (A)$^+$ RNA. Thus, a mRNA of murine intestine in a solution form was obtained.

An aqueous solution containing 1 μl of the mRNA was placed in a 0.5-ml reaction tube, and then incubated at 70° C. for five minutes and cooled to 4° C. The resulting solution was mixed with 2 μl of a 10×RT reaction buffer (an aqueous solution consisting of 200 mM Tris-HCl (pH 8.0) and one mole per liter of potassium chloride), 2 μl of 25 mM magnesium chloride, 2 μl of 100 mM dithiothreitol, 1 μl of 2.5 mM of dNTPs, 1 μl of 0.2 μg/μl random hexamer, 0.5 μl of 35 units/μl "RNasin", a ribonuclease inhibitor commercialized by PROMEGA Co., Ltd., Wisconsin, U.S.A., and 1 μl of 200 units/μl Moloney Murine Leukemia Virus (hereinafter abbreviated as "MMLV"). The mixture solution was brought up to a volume of 20 µl with sterile distilled water, and successively incubated at 25° C. for 10 minutes and at 42° C. for 30 minutes to form a first strand cDNA, followed the incubation at 99° C. for 5 minutes to terminate the reaction.

According to a conventional manner, a consensus sequence was obtained by comparing cDNA sequences of human and rat trehalases, registered under the accession Nos. AB000824 and AF038043, respectively, in "GenBank", a database of nucleic acids provided by the National Institute of Health of USA. The oligonucleotide sequences of SEQ ID NO: 4 and SEQ ID NO: 5 (hereinafter abbreviated as "s1" and "a1", respectively), which had been designed based on the these results, were chemically synthesized in a conventional manner. To a reaction tube, containing the above first strand cDNA solution as a template, were added 5 µl of 10×Pfu reaction buffer, 1 µl of 2.5 units/µl of a Pfu polymerase commercialized by STRATAGENE Co., Ltd., California, U.S.A., 4 µl of 2.5 mM dNTPs, 1 µl of 100 ng/µl oligonucleotide s1 as sense primer, and 1 µl of 100 ng/µl oligonucleotide a1 as an antisense primer. The mixture solution was brought up to a volume of 50 µl with sterile distilled water. The mixture was subjected to a PCR reaction of 35 cycles of successive incubations of at 94° C. for 45 seconds, 52° C. for 45 seconds, and 72° C. for 3.5 minutes.

The PCR reaction product was electrophoresed on 1.2 w/v % agarose gel to give a main band of a DNA of about 1.5 kb. The DNA was extracted and purified on "QIAEX II Gel Extraction Kit", a gel extraction kit commercialized by QIAGEN Co., Ltd., Tokyo, Japan, according to the attached specification.

The purified DNA was ligated to "pCR-Script Amp SK (+)", a plasmid vector, by using "pCR-Script SK (+) Cloning Kit", a cloning kit commercialized by STRATAGENE Co., Ltd., California, U.S.A., according to the attached specification. A part of the ligated product was introduced into "Epicurian Coli XL1-Blue MRF' Kan supercompetent cells", E. coli competent cells attached to the kit, to transform the cells. An appropriate amount of the transformed cells was inoculated to an LB agar plate containing 0.04 mg/ml X-gal and 4 µM of isopropyl thiogalactoside, and the plate was incubated at 37° C. for 16 hours. The formed colonies were respectively suspended in 15 µl portions of sterile distilled water, and the suspensions were heated at 95° C. for 5 minutes and then promptly cooled to 4° C. As mentioned above, the cooled suspensions as templates were subjected to PCR, and the resulting PCR products were subjected to agarose gel electrophoresis. A colony with a DNA of about 1,500 bp was selected and inoculated into 2 ml of LB broth, followed by the incubation at 37° C. for 16 hours under shaking conditions.

A recombinant DNA was extracted from the culture by the usual alkali-SDS method. The DNA was subjected to the usual dideoxy method to analyze a nucleotide sequence and revealed that it contained the nucleotide sequence of SEQ ID NO: 6. The nucleotide sequence was homologous to but not clearly identical to nucleotide sequences of cDNAs of human and rat trehalases. Based on this, the recombinant DNA was confirmed to be a cDNA from murine intestine and named "pCRMTHa".

EXAMPLE 1-2
Isolation of a Partial cDNA from Murine Intestine

The cDNA obtained in Example 1-1 was subjected to 5'RACE, a modified method of PCR, using "5'/3' RACE Kit" commercialized by Roche Diagnostics Co., Ltd., Tokyo, Japan, and this confirmed the existence of a nucleotide sequence which corresponded to the upstream of the 5'-terminal region of the cDNA, followed by isolating a part of the cDNA. Oligonucleotides of SEQ ID Nos. 7 to 9 (hereinafter abbreviated as "a2", "a3", and "a4", respectively) having nucleotide sequences complementary to inner nucleotide sequences in SEQ ID NO: 6, revealed in Example 1-1, were in a conventional manner chemically synthesized for use as antisense primers in this method.

To a 0.5-ml reaction tube, containing 240 ng of the mRNA from murine intestine obtained in Example 1-1, were added 4 µl of a 5×cDNA synthesis solution (an aqueous solution consisting of 250 mM Tris-HCl (pH 8.5), 40 mM magnesium chloride, 150 mM potassium chloride, and 5 mM dithiothreitol), 2 µl of 2.5 mM dNTPs, 1 µl of 91 ng/µl oligonucleotide a2, and 1 µl of 20 units/µl reverse transcriptase from Avian Myeloblastosis Virus (hereinafter abbreviated as "AMV"). The mixture solution was brought up to a volume of 20 µl with sterile distilled water. The mixture was incubated at 55° C. for one hour and at 65° C. for 10 minutes to form a first strand cDNA. The reaction mixture was admixed with 100 µl of a reaction buffer consisting of 3 M guanidine thiocyanate, 10 mM Tris-HCl (pH 6.6), and 5% ethanol. The resulting mixture was transferred to a spin column attached to the above kit, and the spin column was centrifuged at 15,000 rpm for 30 seconds. To the spin column was added 500 µl of a washing buffer containing 20 mM sodium chloride and 2 mM Tris-HCl (pH 7.5) in ethanol, and the contents in the column were washed by centrifuging at 15,000 rpm for 30 seconds. The contents were rewashed with 200 µl of the same washing buffer by centrifugation at 15,000 rpm for 30 seconds. To the column was added 50 µl of an extraction buffer consisting of 10 mM Tris-HCl (pH 8.5) and 1 mM EDTA, and the column was centrifuged at 15,000 rpm for 30 seconds, followed by collecting the extract to obtain a purified first strand cDNA.

To a 0.5-ml reaction tube, containing 19 µl of the above purified first strand cDNAs, were added 2.5 µl of 2 mM dATP and 2.5 µl of a 10×reaction buffer consisting of 100 mM Tris-HCl (pH 8.3), 15 mM magnesium chloride, and 500 mM potassium chloride in distilled water. The mixture was heated at 94° C. for 3 minutes, cooled, admixed with 1 µl of 10 units/µl of a terminal transferase, and successively incubated at 37° C. for 30 minutes and at 72° C. for 10 minutes, followed by binding an oligo-dA to the 3'-terminus of the first strand cDNA. Five microliters of the mixture were transferred to another reaction tube, admixed with 1 µl of 37.5 µM of an oligo-dT anchor primer attached to the kit, 1 µl of 87 ng/µl oligonucleotide a3, 1 µl of 25 mM dNTPs, 1 µl of 2.5 units/µl Pfu polymerase, and 5 µl of a 10×Pfu reaction buffer, and the mixture solution was brought up to a volume of 50 µl with sterile distilled water. The resulting mixture was subjected to a first step PCR of 35 cycles of successive incubations at 94° C. for 45 seconds, 55° C. for 45 seconds, and 72° C. for two minutes.

One microliter of the product in the first step PCR was transferred to another reaction tube, and then admixed with 1 µl of 12.5 µM of a PCR anchor primer, 1 µl of 90 ng/µl oligonucleotide a4, dNTPs, Pfu polymerase, and Pfu reaction buffer similarly as in the first step PCR. The mixture solution was subjected to a second step PCR while controlling temperature similarly as in the first step PCR.

The second step PCR product was electrophoresed on 1.2 w/v % agarose gel in a conventional manner to give a main band of a DNA of about 550 bp. The DNA was extracted and purified on the gel extraction kit similarly as in Example 1-1. In accordance with Example 1-1, the purified DNA was ligated to "pCR-Script Amp SK (+)", a plasmid vector. The ligated product was introduced into *E. coli*, and the recombinant DNA having the desired DNA of about 550 bp was extracted from the transformed cells. The recombinant DNA thus obtained was subjected to the usual dideoxy method and revealed that it contained the nucleotide sequence in SEQ ID NO: 10. The sequence, consisting of 358 bases from after the base 182 in the 3'-terminal region of SEQ ID No: 10, completely coincided with a nucleotide sequence that consisted of 358 bases in the 5'-terminal region of SEQ ID NO: 6, which had been revealed in Example 1-1. Based on this, it was confirmed that the recombinant DNA obtained in this example contained the desired partial cDNA from murine intestine. The recombinant DNA was named "pCRMTHb".

EXAMPLE 1-3

Isolation of a Partial cDNA from Murine Intestine

To confirm the existence of a nucleotide sequence, corresponding to the 3'-terminal downstream region of the cDNA obtained in Example 1-1, and to isolate a cDNA for the nucleotide sequence, the cDNA obtained in Example 1-1 was subjected to 3'RACE, a modified method of PCR, by using "5'/3' RACE Kit" similarly as in Example 1-2. An oligonucleotide consisting of the nucleotide sequence in SEQ ID NO: 11 (hereinafter abbreviated as "s2"), having a nucleotide sequence complementary to an inner sequence in SEQ ID NO: 6 which had been revealed in Example 1-1, was in a conventional manner chemically synthesized as a sense primer used in this method.

To a 0.5-ml reaction tube, containing 240 ng of mRNA from murine intestine obtained in Example 1-1, were added 4 μl of 5×cDNA synthesis buffer as used in Example 1-2, 2μl of 2.5 mM dNTPs, 1 μl of 37.5 μM of an oligo-dT anchor primer, and 1 μl of 20 units/μl of reverse transcriptase from AMV. The mixture solution was brought up to a volume of 20 μl with sterile distilled water, and then successively incubated at 55° C. for one hour and at 65° C. for 10 minutes to obtain a first strand a cDNA.

To a new reaction tube, containing 1 μl of the first strand cDNA, were added 1 μl of 12.5 μM PCR anchor primer, 1 μl of 82 ng/μl oligonucleotide s2, 1 μl of 25 mM dNTPs, 1 μl of 2.5 units/μl Pfu polymerase, and 5 μl of 10×Pfu reaction buffer. The mixture solution was brought up to a volume of 50 μl with sterile distilled water and subjected to a PCR reaction of 35 cycles of successive incubations at 94° C. for 45 seconds, 55° C. for 45 seconds, and 72° C. for two minutes.

The PCR product was electrophoresed on 1.2 w/v % agarose gel in a conventional manner to give a main band of DNA of about 750 bp. The DNA was extracted and purified by using the gel extraction similarly as in Example 1-1. In accordance with Example 1-1, the purified DNA was ligated to "pCR-Script Amp SK(+)", a plasmid vector, and the ligated product was introduced into *E. coli*. The recombinant DNA, which contained the desired DNA of about 750 bp, was extracted from the transformed cells and subjected to the usual dideoxy method, revealing that the DNA contained the nucleotide sequence of SEQ ID NO: 12. A nucleotide sequence, which consisted of 258 bases in the 5'-terminal region in the above nucleotide sequence, completely corresponded to a nucleotide sequence which consisted of 258 bases from after the base 1214 in the 3'-terminal region of SEQ ID NO: 6 which had been revealed in Example 1-1. This revealed that the recombinant DNA in this example contained the desired partial cDNA from murine intestine. The recombinant DNA was named "pCRMTHc".

EXAMPLE 1-4

Preparation of a Full-length cDNA from Murine Intestine pCRMTHa, a recombinant DNA obtained in Example 1-1, had restriction sites of restriction enzymes EcoRI and AccI in the nucleotide sequence of cDNA from murine intestine, and also contained these restriction sites within the nucleotide sequence of the plasmid vector in the downstream of the 3'-terminus. pCRMTHb, a recombinant DNA obtained in Example 1-2, had two restriction sites of EcoRI which corresponded to pCRMTHa. pCRMTHc, a recombinant DNA obtained in Example 1-3, had two restriction sites of AccI which corresponded to pCRMTHa. With these structures, a recombinant DNA, having a full-length of cDNA obtained by linking together the above three types of partial cDNAs, was prepared as indicated below:

About 2.4 μg of the pCRMTHa in Example 1-1 and about 2.4 μg of the pCRMTHb in Example 1-2 were in a conventional manner cleaved with a sufficient amount of a restriction enzyme EcoRI. The digested products were respectively electrophoresed on 1.2 w/v % agarose gel to give bands for DNAs of about 1,150 bp from pCRMTHa and of about 3,500 bp from pCRMTHb. These DNAs were purified after extracted from the agarose gels using a gel extraction kit similarly as in Example 1-1. These two purified DNAs were ligated together with "DNA Ligation Kit version 2", a ligation kit commercialized by Takara Shuzo Co., Ltd., Tokyo, Japan. In accordance with the method in Example 1-1, *E. coli* were transformed with the ligated product. A recombinant DNA having a DNA of about 1,650 bp was extracted from the transformant and named "pCRMTHab".

About 0.8 μg of the pCRMTHa obtained in the above and about 0.8 μg of the pCRMTHc in Example 1-3 were respectively cleaved in a conventional manner with a sufficient amount of a restriction enzyme AccI. The resulting cleaved products were respectively electrophoresed on 1.2 w/v % agarose gel. DNAs of about 4,500 bp from pCRMTHab and about 600 bp from pCRMTHc, which had been separated on the agarose gels, were purified after extracted from the gels using a gel extraction kit similarly as in Example 1-1. These two purified DNAs were ligated using a ligation kit as mentioned above. In accordance with Example 1-1, *E. coli* were transformed with the ligated product. A recombinant DNA having a DNA of about 2,050 bp was extracted from a transformant and named "pCRMTHabc".

The recombinant DNA was subjected to the usual dideoxy method to analyze the nucleotide sequence and revealed that the DNA contained the nucleotide sequence of SEQ ID NO: 3. This nucleotide sequence contained all SEQ ID NOs: 6, 10, and 12, and this confirmed that pCRMTHabc, a recombinant DNA, included the desired ligated cDNA. Thus, a full-length cDNA from murine intestine was obtained. The nucleotide sequence, revealed in this example, encoded an amino acid sequence consisting of 576 amino acids. A coding sequence for the nucleotide sequence of SEQ ID NO: 3 is separately shown in SEQ ID NO: 1.

EXAMPLE 1-5

Production of Polypeptides by Transformants

EXAMPLE 1-5(a)

Preparation of Recombinant DNA

A recombinant DNA for expressing polypeptide was prepared by a PCR method as shown below: The following oligonucleotides were first chemically synthesized; an oligonucleotide in the nucleotide sequence of SEQ ID NO: 13 (hereinafter abbreviated as "s3"), which had been constructed to include nucleotide sequences at the 5'-terminus in SEQ ID NO: 1 and a restriction site by a restriction enzyme of XhoI; and an oligonucleotide in the nucleotide sequence of SEQ ID NO: 14 (hereinafter abbreviated as "a5"), which had been constructed to include nucleotide sequences at the 3'-terminus in SEQ ID NO: 1 and a restriction site by a restriction enzyme of NotI.

To a 0.5-ml reaction tube, containing 2 ng of the recombinant DNA "pCRMTHabc" in Example 1-4, were added 10 µl of 10×Pfu reaction buffer, 1 µl of 2.5 units/µl Pfu polymerase, 1 µl of 25 mM dNTPs, and adequate amounts of oligonucleotides s3 and a5. The mixture solution was brought up to a volume of 100 µl with sterile distilled water, followed by subjecting to a PCR reaction of 40 cycles of successive incubations at 94° C. for 0.5 minutes, 54° C. for 2 minutes, and 72° C. for 3.5 minutes. The resulting PCR product was ligated to "pCR-Script Cam SK(+)", a plasmid vector, by using "pCR-Script Cam SK(+) cloning kit", a cloning kit commercialized by STRATAGENE Co., Ltd., California, U.S.A., according to the attached specification. By using the ligated product, *E. coli* JM109 competent cells, commercialized by Takara Shuzo Co., Ltd., Tokyo, Japan, were transformed in a conventional manner. The transformed cells were inoculated on LB agar plate (pH 7.2) containing 34 µg/ml chloramphenicol, and the plate was incubated at 37° C. for 18 hours. A formed colony was inoculated into 2 ml of a liquid medium with similar composition as above and incubated at 37° C. for 18 hours under shaking conditions. A recombinant DNA was extracted from the culture by the usual alkali-SDS method. The dideoxy method confirmed that the recombinant DNA contained the nucleotide sequence of SEQ ID NO: 1 and a stop codon at the 3'-terminus.

The recombinant DNA thus obtained was in a conventional manner cleaved with restriction enzymes of XhoI and NotI. pCDM8, a plasmid vector commercialized by Invitrogen BV, NV Leek, Netherlands, was similarly cleaved with the above restriction enzymes. These cleaved products were ligated by using "DNA ligation kit version 2", a ligation kit, similarly as in Example 1-4. With the ligated products, *E. coli* MC1061/P3 competent cells, commercialized by Invitrogen BV, NV Leek, Netherlands, were transformed in a conventional manner. The transformed cells were inoculated on LB agar plate (pH 7.2) containing 20 µg/ml ampicillin and 10 µg/ml tetracycline, and the plate was incubated 37° C. for 18 hours. The formed colony was inoculated into 2 ml of a liquid media with similar composition as above and incubated at 37° C. for 18 hours under shaking conditions. A recombinant DNA was extracted from the culture by the usual alkali-SDS method. In the recombinant DNA thus obtained, the DNA of the nucleotide sequence of SEQ ID NO: 1 and a stop codon were ligated in this order to the downstream of a promoter. The recombinant DNA was named "pCDMTH".

EXAMPLE 1-5(b)

Confirmation of Production of Polypeptide and Trehalase Activity

After COS-1 cells (ATCC CRL-1650), a kind of fibroblast cell lines from a kidney of Africa green monkey, were in a conventional manner proliferated to give a prescribed cell concentration, the proliferated cells were transformed by introducing a recombinant DNA, prepared in Example 1-5 (a), into the cells in an amount of 20 µg of "pCDMTH" per $7.5 \times 10^6$ cells by the usual electroporation method. To a flat culture flask was added "Dulbecco's Modified Eagle Medium (Nissui 2)", commercialized by Nissui Pharmaceutical Co., Ltd., Tokyo, Japan, supplemented with 10 w/w % FCS. The transformed COS-1 cells were inoculated to the medium at a rate of $2 \times 10^5$ cells/ml, followed by the incubation at 37° C. for three days in a 5 v/v % $CO_2$ incubator in the usual manner. The culture was in a conventional manner separated into a fraction of cells and a fraction of culture supernatant. The cells were washed by repeating the following procedure for several times: The fraction of cells was suspended in 10 mM sodium phosphate buffer (pH 6.2) and centrifuged at 1,000 rpm and at 4° C. for five minutes, followed by removing the buffer. The fraction of washed cells was admixed with 4% triton X-100 and kept at ambient temperature for 10 minutes. The fraction was centrifuged at 15,000 rpm and at 4° C. for five minutes, followed by collecting a supernatant.

A trehalase activity of the supernatant was examined as follows: The obtained fraction was diluted with 10 mM sodium phosphate buffer (pH 6.2) to give a desired concentration and mixed with α,α-trehalose to give a final concentration of 20 mM. Thereafter, the mixture was incubated at 37° C. for one hour and mixed with 8 v/v % perchloric acid 1/10 volume of the reaction mixture to suspend the reaction. Glucose in the mixture was quantified on "GLUCOSE B-TESTWAKO", a kit for quantifying glucose commercialized by Wako Pure Chemical Industries, Ltd., Osaka, Japan. The amount of α,α-trehalose hydrolyzed in the reaction mixture was calculated based on the change in glucose level before and after the reaction. One unit trehalase activity was defined as an activity of hydrolyzing one µmol of α,α-trehalose per minute. The fraction thus obtained had 2.7 units of trehalase activity. When the above culture supernatant was similarly examined, significant trehalase activity was not detected as found in the supernatant fraction treated with triton X-100. In the case of operating a plasmid vector "pCDM8" instead of the recombinant DNA "pCDMTH" similarly as in this example, no trehalase activity was detected in any fraction.

The results in Examples 1-1 to 1-5 indicate that the nucleotide sequence of SEQ ID NO: 1, contained in "pCDMTH" obtained in this example, encodes a murine trehalase, and this means that the nucleotide sequence is usually contained in a murine trehalase gene. The nucleotide sequence of SEQ ID NO: 1 was compared with other conventional cDNA nucleotide sequences of trehalases with respect to their coincided bases, and this revealed that the nucleotide sequence of the present invention had a highest homology of 94.0% to a cDNA of rat trehalase. The result shows that trehalases of mice and their closely related rodents are encoded by nucleotide sequences with a homology of at least 94.0% to SEQ ID NO: 1.

The result in this example indicates that the murine trehalase is usually expressed as a polypeptide which has an amino acid sequence as shown in parallel in SEQ ID NO: 1 or the amino acid sequence of SEQ ID NO: 2. When examined for amino acid sequence homology based on the number of homologous amino acids, the above amino acid sequence had a homology of 93.5% to that of rat trehalase. Conventional analysis confirmed that hydrophobic amino acids, which are general characteristic signal peptides, were focused on a part that consisted of about 20 amino acids in the N-terminal region of the above amino acid sequence. This indicates that the part of murine trehalase possibly functions as a signal peptide, and a polypeptide other than the part predominantly relates to the expression of trehalase activity.

EXAMPLE 2
Preparation of Polypeptide with Trehalase Activity

A recombinant DNA "pCDMTH" in Example 1-5(a) was transformed by introducing into COS-1 cells by the method in Example 1-5(b). The transformed cells were cultured according to the method in Example 1-5(b), and a fraction of supernatant was obtained from the culture treated with triton X-100. With an index of trehalase activity, the fraction was purified by combining gel filtration chromatography, ion-exchange chromatography, and isoelectric electrophoresis. Accordingly, a polypeptide with trehalase activity was obtained in a relatively-high purity and a yield of 2 mg per liter of culture.

The polypeptide is useful as a standard specimen in the qualitative and quantitative analyses of murine trehalase, an antigen for preparing anti-murine trehalase antibodies, and a material for the antigen as a peptide.

As described above, the present invention is based on the isolation and the structural analysis of both a cDNA, which encodes murine trehalase, and a gene for the cDNA. A variety of DNAs, provided by the present invention, enable to engineer and analyze murine trehalase in a molecular biological manner. For example, according to the present invention, the analysis of trehalase in living bodies such as humans and animals, where the biological roles have not yet been confirmed, can be conducted in a molecular biological manner by using mice useful as animal model. Such an animal model can also be used in researches for treatment, preventive, and diagnostic preparations for diseases such as diseases of trehalose metabolism deficiency caused by deletion or incompletion of trehalase. The DNA of the present invention provides a relatively-large amount of murine trehalase which is valuable in conducting the above analysis. Trehalase would be a main enzyme which relates to the hydrolysis and metabolism of trehalose in living bodies. Accordingly, the present invention would provide trehalase and important information in elucidating unknown physiological functions of trehalose in the bodies of mammals and humans.

Thus, the present invention having these outstanding functions and effects is a significant invention that would greatly contribute to this art.

While what are at present considered to be the preferred embodiments of the invention have been described, it will be understood that various modifications may be made therein, and the appended claims are intended to cover all such modifications as fall within the true spirits and scope of the invention.

We claim:

1. An isolated DNA which comprises the nucleotide sequence of SEQ ID NO:1 encoding a mouse trehalase or its complementary nucleotide sequence.

2. The DNA of claim 1, which is carried on an autonomously-replicable vector.

3. A transformed cell obtained by introducing the DNA of claim 2, into an appropriate host cell derived from a microorganism, plant or animal.

4. A process for producing a polypeptide, comprising:
allowing a transformed cell of claim 3 to express a polypeptide encoded by the DNA; and
collecting the expressed polypeptide.

5. An isolated DNA which encodes the amino acid sequence of SEQ ID NO:2 or its complementary nucleotide sequence.

6. An isolated DNA of claim 5, which encodes the amino acid residues 20 to 576 of SEQ ID NO:2.

7. The DNA of claim 6, which is carried on an autonomously-replicable vector.

8. A transformed cell obtained by introducing the DNA of claim 7 into an appropriate host cell derived from a microorganism, plant or animal.

9. A process for producing a polypeptide, comprising:
allowing a transformed cell of claim 8 to express a polypeptide encoded by the DNA; and
collecting the expressed polypeptide.

10. The DNA of claim 5, which is carried on an autonomously-replicable vector.

11. A transformed cell obtained by introducing the DNA of claim 10 into an appropriate host cell derived from a microorganism, plant or animal.

12. A process for producing a polypeptide, comprising:
    allowing a transformed cell of claim 11 to express a polypeptide encoded by the DNA; and
    collecting the expressed polypeptide.

13. An isolated mouse trehalase exon DNA, which comprises a member selected from the group consisting of nucleotides 1–80, 81–181, 182–326, 327–414, 415–515, 516–608, 609–725, 726–848, 849–898, 899–1093, 1094–1311, 1312–1423, 1424–1536, 1537–1590, and 1591–1728 in the nucleotide sequence of SEQ ID NO:1.

14. The DNA of claim 13, which is carried on an autonomously-replicable vector.

15. A transformed cell obtained by introducing the DNA of claim 14 into an appropriate host cell derived from a microorganism, plant or animal.

* * * * *

SEQUENCE LISTING

<160> NUMBER OF SEQ ID NOS: 14

<210> SEQ ID NO 1
<211> LENGTH: 1728
<212> TYPE: DNA
<213> ORGANISM: mouse

<400> SEQUENCE: 1

```
atg acc tgg gag ctg cac ctg ctg ctt ctg ctg ggg ctg gga ctt agg     48
Met Thr Trp Glu Leu His Leu Leu Leu Leu Leu Gly Leu Gly Leu Arg
            5                  10                  15 tcc cag gag gcc ctg cca cca ccc tgt gag agc cag atc tac tgc cat     96
Ser Gln Glu Ala Leu Pro Pro Pro Cys Glu Ser Gln Ile Tyr Cys His
        20                  25                  30 gga gag ctc ctg cac caa gtt cag atg gcc cag ctc tac caa gat gac    144
Gly Glu Leu Leu His Gln Val Gln Met Ala Gln Leu Tyr Gln Asp Asp
            35                  40                  45 aag cag ttt gtg gat atg tca ctg gcc aca tct cca gat gaa gtc ctg    192
Lys Gln Phe Val Asp Met Ser Leu Ala Thr Ser Pro Asp Glu Val Leu
    50                  55                  60 cag aag ttc agt gag ctg gcc aca gtc cac aac cac agc atc ccc aag    240
Gln Lys Phe Ser Glu Leu Ala Thr Val His Asn His Ser Ile Pro Lys
65                  70                  75                  80 gaa cag ctt cag gaa ttt gtc cag agt cac ttc cag ccc gtg ggg cag    288
Glu Gln Leu Gln Glu Phe Val Gln Ser His Phe Gln Pro Val Gly Gln
                85                  90                  95 gag ctg cag tcc tgg acc cct gag gac tgg aag gac agc cct cag ttc    336
Glu Leu Gln Ser Trp Thr Pro Glu Asp Trp Lys Asp Ser Pro Gln Phe
            100                 105                 110 ctg cag aag atc tcg gat gct aat ctg cgt gtc tgg gcg gag gag cta    384
Leu Gln Lys Ile Ser Asp Ala Asn Leu Arg Val Trp Ala Glu Glu Leu
        115                 120                 125 cac aag atc tgg aaa aag ctg gga aag aag atg aaa gca gaa gtc ctc    432
His Lys Ile Trp Lys Lys Leu Gly Lys Lys Met Lys Ala Glu Val Leu
    130                 135                 140
```

```
agc tac ccc gag agg tcc tcc cta atc tac tca aag cac ccc ttc att    480
Ser Tyr Pro Glu Arg Ser Ser Leu Ile Tyr Ser Lys His Pro Phe Ile
145                 150                 155                 160 gtg ccc ggg ggg cgc ttt gtt gaa ttc tac tac tgg gac tcg tac tgg    528
Val Pro Gly Gly Arg Phe Val Glu Phe Tyr Tyr Trp Asp Ser Tyr Trp
            165                 170                 175 gtg atg gaa ggc ctg ctt ctt tct gag atg gcc tca aca gtg aag ggt    576
Val Met Glu Gly Leu Leu Leu Ser Glu Met Ala Ser Thr Val Lys Gly
        180                 185                 190 atg ctg cag aac ttt ctg gat ctg gtg aag acc tac gga cat atc ccc    624
Met Leu Gln Asn Phe Leu Asp Leu Val Lys Thr Tyr Gly His Ile Pro
    195                 200                 205 aac ggt gga cgc ata tat tac ctg caa cgg agc cag ccc cca ctc ctg    672
Asn Gly Gly Arg Ile Tyr Tyr Leu Gln Arg Ser Gln Pro Pro Leu Leu
210                 215                 220 act ctc atg atg gat cga tat gta gct cat acc aag gat gtc gcc ttc    720
Thr Leu Met Met Asp Arg Tyr Val Ala His Thr Lys Asp Val Ala Phe
225                 230                 235                 240 ctt cag gag aat att ggg act cta gcc tct gaa ctg gac ttc tgg act    768
Leu Gln Glu Asn Ile Gly Thr Leu Ala Ser Glu Leu Asp Phe Trp Thr
            245                 250                 255 gtg aac agg act gtc tct gta gtc tca gga gga caa agc tat gtc tta    816
Val Asn Arg Thr Val Ser Val Val Ser Gly Gly Gln Ser Tyr Val Leu
        260                 265                 270 aat cgc tac tat gtc cct tat ggg gga ccc agg cca gag tcc tac agg    864
Asn Arg Tyr Tyr Val Pro Tyr Gly Gly Pro Arg Pro Glu Ser Tyr Arg
    275                 280                 285 aaa gac gca gaa ttg gca aac tct gtg cca gaa ggg gac cga gag act    912
Lys Asp Ala Glu Leu Ala Asn Ser Val Pro Glu Gly Asp Arg Glu Thr
290                 295                 300 ctg tgg gct gag ctc aag gct ggg gct gag tct ggc tgg gac ttc tct    960
Leu Trp Ala Glu Leu Lys Ala Gly Ala Glu Ser Gly Trp Asp Phe Ser
305                 310                 315                 320 tca cgc tgg ctt gtt gga gga cca gac cct gat ttg ctc agc agc atc    1008
Ser Arg Trp Leu Val Gly Gly Pro Asp Pro Asp Leu Leu Ser Ser Ile
            325                 330                 335 cga acc agc aaa atg gta ccc gct gat ctg aac gcg ttc ctg tgc caa    1056
Arg Thr Ser Lys Met Val Pro Ala Asp Leu Asn Ala Phe Leu Cys Gln
        340                 345                 350 gca gag gaa ctg atg agt aac ttc tac tcc aga cta ggg aac gac aca    1104
Ala Glu Glu Leu Met Ser Asn Phe Tyr Ser Arg Leu Gly Asn Asp Thr
    355                 360                 365 gag gcc aca aag tac agg aac ctg cgg gcc cag cgc ttg gcc gcc atg    1152
Glu Ala Thr Lys Tyr Arg Asn Leu Arg Ala Gln Arg Leu Ala Ala Met
370                 375                 380 gaa gct gtc ctg tgg gac gag cag aag ggt gcc tgg ttt gac tat gac    1200
Glu Ala Val Leu Trp Asp Glu Gln Lys Gly Ala Trp Phe Asp Tyr Asp
385                 390                 395                 400 ttg gaa aag ggg aag aag aac ctg gag ttt tat ccc tcc aac ctc tcc    1248
Leu Glu Lys Gly Lys Lys Asn Leu Glu Phe Tyr Pro Ser Asn Leu Ser
            405                 410                 415 cca ctt tgg gct ggc tgc ttc tca gac cct agt gtt gct gac aag gct    1296
Pro Leu Trp Ala Gly Cys Phe Ser Asp Pro Ser Val Ala Asp Lys Ala
        420                 425                 430 ctg aag tac ttg gag gac agc aag atc ttg acc tac caa tat gga atc    1344
Leu Lys Tyr Leu Glu Asp Ser Lys Ile Leu Thr Tyr Gln Tyr Gly Ile
    435                 440                 445 cca acc tct ctt cgt aac aca ggc cag cag tgg gac ttc ccc aat gcc    1392
Pro Thr Ser Leu Arg Asn Thr Gly Gln Gln Trp Asp Phe Pro Asn Ala
450                 455                 460
```

```
tgg gcc cca ctg cag gac ctg gtc att aga ggt ttg gcc aag tca gct    1440
Trp Ala Pro Leu Gln Asp Leu Val Ile Arg Gly Leu Ala Lys Ser Ala
465                 470                 475                 480 tcc ccc cgg act cag gag gtg gct ttc cag ctg gcc cag aat tgg atc    1488
Ser Pro Arg Thr Gln Glu Val Ala Phe Gln Leu Ala Gln Asn Trp Ile
                485                 490                 495 aaa acc aac ttc aaa gtc tac tcc caa aag tca gcg atg ttt gag aag    1536
Lys Thr Asn Phe Lys Val Tyr Ser Gln Lys Ser Ala Met Phe Glu Lys
            500                 505                 510 tat gac atc agc aac ggt gga cat cca ggt gga gga ggg gag tat gaa    1584
Tyr Asp Ile Ser Asn Gly Gly His Pro Gly Gly Gly Gly Glu Tyr Glu
        515                 520                 525 gtt cag gaa gga ttt ggc tgg aca aac gga ttg gcc ctg atg ctt ctg    1632
Val Gln Glu Gly Phe Gly Trp Thr Asn Gly Leu Ala Leu Met Leu Leu
    530                 535                 540 gat cgc tat ggt gac cag ttg act tca ggg acc cag tta gct tcc ctg    1680
Asp Arg Tyr Gly Asp Gln Leu Thr Ser Gly Thr Gln Leu Ala Ser Leu
545                 550                 555                 560 gga ccc cac tgc cta gtg gct gcc ctt ctt ctc agt ctt ctg cta cag    1728
Gly Pro His Cys Leu Val Ala Ala Leu Leu Leu Ser Leu Leu Leu Gln
                565                 570                 575

<210> SEQ ID NO 2
<211> LENGTH: 576
<212> TYPE: PRT
<213> ORGANISM: mouse

<400> SEQUENCE: 2

Met Thr Trp Glu Leu His Leu Leu Leu Leu Gly Leu Gly Leu Arg
                5                   10                  15

Ser Gln Glu Ala Leu Pro Pro Cys Glu Ser Gln Ile Tyr Cys His
            20                  25                  30

Gly Glu Leu Leu His Gln Val Gln Met Ala Gln Leu Tyr Gln Asp Asp
        35                  40                  45

Lys Gln Phe Val Asp Met Ser Leu Ala Thr Ser Pro Asp Glu Val Leu
    50                  55                  60

Gln Lys Phe Ser Glu Leu Ala Thr Val His Asn His Ser Ile Pro Lys
65                  70                  75                  80

Glu Gln Leu Gln Glu Phe Val Gln Ser His Phe Gln Pro Val Gly Gln
                85                  90                  95

Glu Leu Gln Ser Trp Thr Pro Glu Asp Trp Lys Asp Ser Pro Gln Phe
            100                 105                 110

Leu Gln Lys Ile Ser Asp Ala Asn Leu Arg Val Trp Ala Glu Glu Leu
        115                 120                 125

His Lys Ile Trp Lys Lys Leu Gly Lys Lys Met Lys Ala Glu Val Leu
    130                 135                 140

Ser Tyr Pro Glu Arg Ser Ser Leu Ile Tyr Ser Lys His Pro Phe Ile
145                 150                 155                 160

Val Pro Gly Gly Arg Phe Val Glu Phe Tyr Tyr Trp Asp Ser Tyr Trp
                165                 170                 175

Val Met Glu Gly Leu Leu Leu Ser Glu Met Ala Ser Thr Val Lys Gly
            180                 185                 190

Met Leu Gln Asn Phe Leu Asp Leu Val Lys Thr Tyr Gly His Ile Pro
        195                 200                 205

Asn Gly Gly Arg Ile Tyr Tyr Leu Gln Arg Ser Gln Pro Pro Leu Leu
    210                 215                 220
```

```
Thr Leu Met Met Asp Arg Tyr Val Ala His Thr Lys Asp Val Ala Phe
225                 230                 235                 240

Leu Gln Glu Asn Ile Gly Thr Leu Ala Ser Glu Leu Asp Phe Trp Thr
            245                 250                 255

Val Asn Arg Thr Val Ser Val Ser Gly Gly Gln Ser Tyr Val Leu
            260                 265                 270

Asn Arg Tyr Tyr Val Pro Tyr Gly Gly Pro Arg Pro Glu Ser Tyr Arg
        275                 280                 285

Lys Asp Ala Glu Leu Ala Asn Ser Val Pro Gly Asp Arg Glu Thr
    290                 295                 300

Leu Trp Ala Glu Leu Lys Ala Gly Ala Glu Ser Gly Trp Asp Phe Ser
305                 310                 315                 320

Ser Arg Trp Leu Val Gly Gly Pro Asp Pro Asp Leu Leu Ser Ser Ile
                325                 330                 335

Arg Thr Ser Lys Met Val Pro Ala Asp Leu Asn Ala Phe Leu Cys Gln
                340                 345                 350

Ala Glu Glu Leu Met Ser Asn Phe Tyr Ser Arg Leu Gly Asn Asp Thr
            355                 360                 365

Glu Ala Thr Lys Tyr Arg Asn Leu Arg Ala Gln Arg Leu Ala Ala Met
    370                 375                 380

Glu Ala Val Leu Trp Asp Glu Gln Lys Gly Ala Trp Phe Asp Tyr Asp
385                 390                 395                 400

Leu Glu Lys Gly Lys Lys Asn Leu Glu Phe Tyr Pro Ser Asn Leu Ser
                405                 410                 415

Pro Leu Trp Ala Gly Cys Phe Ser Asp Pro Ser Val Ala Asp Lys Ala
                420                 425                 430

Leu Lys Tyr Leu Glu Asp Ser Lys Ile Leu Thr Tyr Gln Tyr Gly Ile
            435                 440                 445

Pro Thr Ser Leu Arg Asn Thr Gly Gln Gln Trp Asp Phe Pro Asn Ala
    450                 455                 460

Trp Ala Pro Leu Gln Asp Leu Val Ile Arg Gly Leu Ala Lys Ser Ala
465                 470                 475                 480

Ser Pro Arg Thr Gln Glu Val Ala Phe Gln Leu Ala Gln Asn Trp Ile
                485                 490                 495

Lys Thr Asn Phe Lys Val Tyr Ser Gln Lys Ser Ala Met Phe Glu Lys
                500                 505                 510

Tyr Asp Ile Ser Asn Gly Gly His Pro Gly Gly Gly Glu Tyr Glu
            515                 520                 525

Val Gln Glu Gly Phe Gly Trp Thr Asn Gly Leu Ala Leu Met Leu Leu
    530                 535                 540

Asp Arg Tyr Gly Asp Gln Leu Thr Ser Gly Thr Gln Leu Ala Ser Leu
545                 550                 555                 560

Gly Pro His Cys Leu Val Ala Ala Leu Leu Leu Ser Leu Leu Leu Gln
                565                 570                 575

<210> SEQ ID NO 3
<211> LENGTH: 2045
<212> TYPE: DNA
<213> ORGANISM: mouse
<220> FEATURE:
<221> NAME/KEY: CDS
<222> LOCATION: (24)...(1751)

<400> SEQUENCE: 3
ccgttctagg caccgtgccc agg atg acc tgg gag ctg cac ctg ctg ctt ctg     53
                          Met Thr Trp Glu Leu His Leu Leu Leu Leu
```

-continued

```
                          5                           10
ctg ggg ctg gga ctt agg tcc cag gag gcc ctg cca cca ccc tgt gag      101
Leu Gly Leu Gly Leu Arg Ser Gln Glu Ala Leu Pro Pro Pro Cys Glu
                         15                   20                 25 agc cag atc tac tgc cat gga gag ctc ctg cac caa gtt cag atg gcc      149
Ser Gln Ile Tyr Cys His Gly Glu Leu Leu His Gln Val Gln Met Ala
             30                  35                   40 cag ctc tac caa gat gac aag cag ttt gtg gat atg tca ctg gcc aca      197
Gln Leu Tyr Gln Asp Asp Lys Gln Phe Val Asp Met Ser Leu Ala Thr
             45                  50                  55 tct cca gat gaa gtc ctg cag aag ttc agt gag ctg gcc aca gtc cac      245
Ser Pro Asp Glu Val Leu Gln Lys Phe Ser Glu Leu Ala Thr Val His
         60                  65                  70 aac cac agc atc ccc aag gaa cag ctt cag gaa ttt gtc cag agt cac      293
Asn His Ser Ile Pro Lys Glu Gln Leu Gln Glu Phe Val Gln Ser His
75                  80                  85                  90 ttc cag ccc gtg ggg cag gag ctg cag tcc tgg acc cct gag gac tgg      341
Phe Gln Pro Val Gly Gln Glu Leu Gln Ser Trp Thr Pro Glu Asp Trp
                 95                 100                 105 aag gac agc cct cag ttc ctg cag aag atc tcg gat gct aat ctg cgt      389
Lys Asp Ser Pro Gln Phe Leu Gln Lys Ile Ser Asp Ala Asn Leu Arg
             110                 115                 120 gtc tgg gcg gag gag cta cac aag atc tgg aaa aag ctg gga aag aag      437
Val Trp Ala Glu Glu Leu His Lys Ile Trp Lys Lys Leu Gly Lys Lys
         125                 130                 135 atg aaa gca gaa gtc ctc agc tac ccc gag agg tcc tcc cta atc tac      485
Met Lys Ala Glu Val Leu Ser Tyr Pro Glu Arg Ser Ser Leu Ile Tyr
     140                 145                 150 tca aag cac ccc ttc att gtg ccc ggg ggc cgc ttt gtt gaa ttc tac      533
Ser Lys His Pro Phe Ile Val Pro Gly Gly Arg Phe Val Glu Phe Tyr
155                 160                 165                 170 tac tgg gac tcg tac tgg gtg atg gaa ggc ctg ctt ctt tct gag atg      581
Tyr Trp Asp Ser Tyr Trp Val Met Glu Gly Leu Leu Leu Ser Glu Met
                 175                 180                 185 gcc tca aca gtg aag ggt atg ctg cag aac ttt ctg gat ctg gtg aag      629
Ala Ser Thr Val Lys Gly Met Leu Gln Asn Phe Leu Asp Leu Val Lys
             190                 195                 200 acc tac gga cat atc ccc aac ggt gga cgc ata tat tac ctg caa cgg      677
Thr Tyr Gly His Ile Pro Asn Gly Gly Arg Ile Tyr Tyr Leu Gln Arg
         205                 210                 215 agc cag ccc cca ctc ctg act ctc atg atg gat cga tat gta gct cat      725
Ser Gln Pro Pro Leu Leu Thr Leu Met Met Asp Arg Tyr Val Ala His
     220                 225                 230 acc aag gat gtc gcc ttc ctt cag gag aat att ggg act cta gcc tct      773
Thr Lys Asp Val Ala Phe Leu Gln Glu Asn Ile Gly Thr Leu Ala Ser
235                 240                 245                 250 gaa ctg gac ttc tgg act gtg aac agg act gtc tct gta gtc tca gga      821
Glu Leu Asp Phe Trp Thr Val Asn Arg Thr Val Ser Val Val Ser Gly
                 255                 260                 265 gga caa agc tat gtc tta aat cgc tac tat gtc cct tat ggg gga ccc      869
Gly Gln Ser Tyr Val Leu Asn Arg Tyr Tyr Val Pro Tyr Gly Gly Pro
             270                 275                 280 agg cca gag tcc tac agg aaa gac gca gaa ttg gca aac tct gtg cca      917
Arg Pro Glu Ser Tyr Arg Lys Asp Ala Glu Leu Ala Asn Ser Val Pro
         285                 290                 295 gaa ggg gac cga gag act ctg tgg gct gag ctc aag gct ggg gct gag      965
Glu Gly Asp Arg Glu Thr Leu Trp Ala Glu Leu Lys Ala Gly Ala Glu
     300                 305                 310 tct ggc tgg gac ttc tct tca cgc tgg ctt gtt gga ggc cca gac cct     1013
```

```
Ser Gly Trp Asp Phe Ser Ser Arg Trp Leu Val Gly Pro Asp Pro
315                 320                 325                 330 gat ttg ctc agc agc atc cga acc agc aaa atg gta ccc gct gat ctg    1061
Asp Leu Leu Ser Ser Ile Arg Thr Ser Lys Met Val Pro Ala Asp Leu
                    335                 340                 345 aac gcg ttc ctg tgc caa gca gag gaa ctg atg agt aac ttc tac tcc    1109
Asn Ala Phe Leu Cys Gln Ala Glu Glu Leu Met Ser Asn Phe Tyr Ser
            350                 355                 360 aga cta ggg aac gac aca gag gcc aca aag tac agg aac ctg cgg gcc    1157
Arg Leu Gly Asn Asp Thr Glu Ala Thr Lys Tyr Arg Asn Leu Arg Ala
        365                 370                 375 cag cgc ttg gcc gcc atg gaa gct gtc ctg tgg gac gag cag aag ggt    1205
Gln Arg Leu Ala Ala Met Glu Ala Val Leu Trp Asp Glu Gln Lys Gly
    380                 385                 390 gcc tgg ttt gac tat gac ttg gaa aag ggg aag aag aac ctg gag ttt    1253
Ala Trp Phe Asp Tyr Asp Leu Glu Lys Gly Lys Lys Asn Leu Glu Phe
395                 400                 405                 410 tat ccc tcc aac ctc tcc cca ctt tgg gct ggc tgc ttc tca gac cct    1301
Tyr Pro Ser Asn Leu Ser Pro Leu Trp Ala Gly Cys Phe Ser Asp Pro
                    415                 420                 425 agt gtt gct gac aag gct ctg aag tac ttg gag gac agc aag atc ttg    1349
Ser Val Ala Asp Lys Ala Leu Lys Tyr Leu Glu Asp Ser Lys Ile Leu
            430                 435                 440 acc tac caa tat gga atc cca acc tct ctt cgt aac aca ggc cag cag    1397
Thr Tyr Gln Tyr Gly Ile Pro Thr Ser Leu Arg Asn Thr Gly Gln Gln
        445                 450                 455 tgg gac ttc ccc aat gcc tgg gcc cca ctg cag gac ctg gtc att aga    1445
Trp Asp Phe Pro Asn Ala Trp Ala Pro Leu Gln Asp Leu Val Ile Arg
    460                 465                 470 ggt ttg gcc aag tca gct tcc ccc cgg act cag gag gtg gct ttc cag    1493
Gly Leu Ala Lys Ser Ala Ser Pro Arg Thr Gln Glu Val Ala Phe Gln
475                 480                 485                 490 ctg gcc cag aat tgg atc aaa acc aac ttc aaa gtc tac tcc caa aag    1541
Leu Ala Gln Asn Trp Ile Lys Thr Asn Phe Lys Val Tyr Ser Gln Lys
                    495                 500                 505 tca gcg atg ttt gag aag tat gac atc agc aac ggt gga cat cca ggt    1589
Ser Ala Met Phe Glu Lys Tyr Asp Ile Ser Asn Gly Gly His Pro Gly
            510                 515                 520 gga gga ggg gag tat gaa gtt cag gaa gga ttt ggc tgg aca aac gga    1637
Gly Gly Gly Glu Tyr Glu Val Gln Glu Gly Phe Gly Trp Thr Asn Gly
        525                 530                 535 ttg gcc ctg atg ctt ctg gat cgc tat ggt gac cag ttg act tca ggg    1685
Leu Ala Leu Met Leu Leu Asp Arg Tyr Gly Asp Gln Leu Thr Ser Gly
    540                 545                 550 acc cag tta gct tcc ctg gga ccc cac tgc cta gtg gct gcc ctt ctt    1733
Thr Gln Leu Ala Ser Leu Gly Pro His Cys Leu Val Ala Ala Leu Leu
555                 560                 565                 570 ctc agt ctt ctg cta cag tgacaagaac aagaatggac tcactgcctg           1781
Leu Ser Leu Leu Leu Gln
                575 cgctttctcc cctggcccca gctcatggtt cattaaaccc ttgctctacc ttcccttata    1841 gccccacccc caccatgccc cttcctgctc ataatgtgtc ctgagccaag aagtgaccaa    1901 gaggtcaaga ctgtaatttt cacagtgttc tgagccaaga agtgaccaag aggtcaaggt    1961 tgtaattttc acgagggcgg aaactgaatc ctgataccta agtatccta tcgggtacca     2021 aatatagctc agagttccac actc                                           2045

<210> SEQ ID NO 4
```

```
<211> LENGTH: 20
<212> TYPE: DNA
<213> ORGANISM: Artificial Sequence
<220> FEATURE:
<223> OTHER INFORMATION: Designed oligonucleotide based on conserved
      nucleotide sequences in cDNAs for human and rat trehalase

<400> SEQUENCE: 4
gatgacaagc agtttgtgga                                                  20

<210> SEQ ID NO 5
<211> LENGTH: 18
<212> TYPE: DNA
<213> ORGANISM: Artificial Sequence
<220> FEATURE:
<223> OTHER INFORMATION: Designed oligonucleotide based on conserved
      nucleotide sequences in cDNAs for human and rat trehalase

<400> SEQUENCE: 5
gtcaccatag cggtccag                                                    18

<210> SEQ ID NO 6
<211> LENGTH: 1471
<212> TYPE: DNA
<213> ORGANISM: mouse

<400> SEQUENCE: 6
tatgtcactg gccacatctc cagatgaagt cctgcagaag ttcagtgagc tggccacagt        60
ccacaaccac agcatcccca aggaacagct tcaggaattt gtccagagtc acttccagcc       120
cgtggggcag gagctgcagt cctggacccc tgaggactgg aaggacagcc ctcagttcct       180
gcagaagatc tcggatgcta atctgcgtgt ctgggcggag gagctacaca agatctggaa       240
aaagctggga agaagatga aagcagaagt cctcagctac cccgagaggt cctccctaat        300
ctactcaaag cacccccttca ttgtgcccgg gggcgctttt gttgaattct actactggga     360
ctcgtactgg gtgatggaag cctgcttct ttctgagatg gcctcaacag tgaagggtat       420
gctgcagaac tttctggatc tggtgaagac ctacggacat atccccaacg gtggacgcat      480
atattacctg caacggagcc agcccccact cctgactctc atgatggatc gatatgtagc      540
tcataccaag gatgtcgcct tccttcagga gaatattggg actctagcct gaactgga       600 cttctggact gtgaacagga ctgtctctgt agtctcagga ggacaaagct atgtcttaaa      660
tcgctactat gtcccttatg ggggacccag gccagtcc tacaggaaag acgcagaatt       720
ggcaaactct gtgccagaag gggaccgaga gactctgtgg gctgagctca aggctgggc       780 tgagtctggc tgggacttct cttcacgctg gcttgttgga ggcccagacc tgatttgct     840 cagcagcatc cgaaccagca aatggtacc cgctgatctg aacgcgttcc tgtgccaagc     900
agaggaactg atgagtaact tctactccag actagggaac gacacagagg ccacaaagta     960
caggaacctg cgggcccagc gcttggccgc catggaagct gtcctgtggg acgagcagaa    1020
gggtgcctgg tttgactatg acttggaaaa ggggaagaag aacctggagt tttatccctc    1080
caacctctcc ccactttggg ctggctgctt ctcagaccct agtgttgctg acaaggctct    1140
gaagtacttg gaggacagca agatcttgac ctaccaatat ggaatcccaa cctctcttcg    1200
taacacaggc cagcagtggg acttccccaa tgcctgggcc ccactgcagg acctggtcat    1260 tagaggttttg gccaagtcag cttcccccccg gactcaggag gtggctttcc agctggccca    1320
gaattggatc aaaaccaact tcaaagtcta ctcccaaaag tcagcgatgt ttgagaagta    1380
tgacatcagc aacggtggac atccaggtgg aggagggggag tatgaagttc aggaaggatt    1440
```
tggctggaca aacggattgg ccctgatgct t                                         1471

<210> SEQ ID NO 7
<211> LENGTH: 22
<212> TYPE: DNA
<213> ORGANISM: Artificial Sequence
<220> FEATURE:
<223> OTHER INFORMATION: Designed oligonucleotide to have complementary
      sequence to internal part of SEQ ID NO:6

<400> SEQUENCE: 7
tatgtccgta gttcttcacc ag                                                     22

<210> SEQ ID NO 8
<211> LENGTH: 21
<212> TYPE: DNA
<213> ORGANISM: Artificial Sequence
<220> FEATURE:
<223> OTHER INFORMATION: Designed oligonucleotide to have complementary
      sequence to internal part of SEQ ID NO:6

<400> SEQUENCE: 8
gcagcatacc cttcactgtt g                                                      21

<210> SEQ ID NO 9
<211> LENGTH: 21
<212> TYPE: DNA
<213> ORGANISM: Artificial Sequence
<220> FEATURE:
<223> OTHER INFORMATION: Designed oligonucleotide to have complementary
      sequence to internal part of SEQ ID NO:6

<400> SEQUENCE: 9
ttccatcacc cagtacgagt c                                                      21

<210> SEQ ID NO 10
<211> LENGTH: 539
<212> TYPE: DNA
<213> ORGANISM: mouse

<400> SEQUENCE: 10
ccgttctagg caccgtgccc aggatgacct gggagctgca cctgctgctt ctgctggggc           60
tgggacttag gtcccaggag gccctgccac caccctgtga gagccagatc tactgccatg          120
gagagctcct gcaccaagtt cagatggccc agctctacca agatgacaag cagtttgtgg          180
atatgtcact ggccacatct ccagatgaag tcctgcagaa gttcagtgag ctggccacag          240
tccacaacca cagcatcccc aaggaacagc ttcaggaatt tgtccagagt cacttccagc          300
ccgtggggca ggagctgcag tcctggaccc ctgaggactg gaaggacagc cctcagttcc          360
tgcagaagat ctcggatgct aatctgcgtg tctgggcgga ggagctacac aagatctgga          420
aaaagctggg aaagaagatg aaagcagaag tcctcagcta ccccgagagg tcctccctaa          480
tctactcaaa gcacccctcc attgtgcccg gggggcgctt tgttgaattc tactactgg           539

<210> SEQ ID NO 11
<211> LENGTH: 20
<212> TYPE: DNA
<213> ORGANISM: Artificial Sequence
<220> FEATURE:
<223> OTHER INFORMATION: Designed oligonucleotide to have internal
      sequence of SEQ ID NO:6

<400> SEQUENCE: 11

-continued

```
ttcttcgtaa cacaggccag                                                    20

<210> SEQ ID NO 12
<211> LENGTH: 651
<212> TYPE: DNA
<213> ORGANISM: mouse

<400> SEQUENCE: 12
cagtgggact tccccaatgc ctgggcccca ctgcaggacc tggtcattag aggtttggcc        60
aagtcagctt ccccccggac tcaggaggtg gctttccagc tggcccagaa ttggatcaaa       120
accaacttca aagtctactc ccaaaagtca gcgatgtttg agaagtatga catcagcaac       180
ggtggacatc caggtggagg aggggagtat gaagttcagg aaggatttgg ctggacaaac       240
ggattggccc tgatgcttct ggatcgctat ggtgaccagt tgacttcagg gacccagtta       300
gcttccctgg gacccactg cctagtggct gcccttcttc tcagtcttct gctacagtga       360
caagaacaag aatggactca ctgcctgcgc tttctcccct ggcccagct catggttcat        420 taaaccttg ctctaccttc ccttatagcc ccacccccac catgcccctt cctgctcata        480
atgtgtcctg agccaagaag tgaccaagag gtcaagactg taattttcac agtgttctga      540
gccaagaagt gaccaagagg tcaaggttgt aattttcacg agggcggaaa ctgaatcctg      600
atacctaaag tatcctatcg ggtaccaaat atagctcaga gttccacact c               651

<210> SEQ ID NO 13
<211> LENGTH: 28
<212> TYPE: DNA
<213> ORGANISM: Artificial Sequence
<220> FEATURE:
<223> OTHER INFORMATION: Designed oligonucleotide to contain 5'-terminal
      sequence of SEQ ID NO:1 and Xho I recognition site

<400> SEQUENCE: 13
aatctcgagc caccatgacc tgggagct                                           28

<210> SEQ ID NO 14
<211> LENGTH: 29
<212> TYPE: DNA
<213> ORGANISM: Artificial Sequence
<220> FEATURE:
<223> OTHER INFORMATION: Designed oligonucleotide to contain
      complementary sequence to 3'-terminal of SEQ ID NO:1 and Not I
      recognition site

<400> SEQUENCE: 14
tctgcggccg cttactgtag cagaagact                                          29
```